United States Patent [19]

Tsujimoto et al.

[11] 4,069,155
[45] Jan. 17, 1978

[54] HEMODIALYSIS SYSTEM

[75] Inventors: Yasuhiro Tsujimoto, Toyonaka; Junichi Azuma, Hirakata; Yoshihiko Matsumura, Kawanishi; Katsumi Noda, Takatsuki, all of Japan

[73] Assignee: Takeda Chemical Industries, Ltd., Japan

[21] Appl. No.: 692,024

[22] Filed: June 1, 1976

[30] Foreign Application Priority Data

May 29, 1975 Japan .................................. 50-65105

[51] Int. Cl.$^2$ ............................................. B01D 13/00
[52] U.S. Cl. ........................... 210/195 R; 210/257 M; 210/258; 210/321 B
[58] Field of Search ............... 210/22, 96 M, 194–197, 210/257 M, 258, 321 B

[56] References Cited

U.S. PATENT DOCUMENTS

| 3,406,826 | 10/1968 | Willock | 210/321 B X |
|---|---|---|---|
| 3,506,126 | 4/1970 | Serfass et al. | 210/195 R X |
| 3,527,700 | 9/1970 | Goldhaber | 210/22 |
| 3,598,727 | 8/1971 | Willock | 210/321 B X |
| 3,626,670 | 12/1971 | Pecker | 210/321 B X |
| 3,669,880 | 6/1972 | Marantz et al. | 210/22 |
| 3,697,418 | 10/1972 | Johnson | 210/195 R X |
| 3,722,680 | 3/1973 | Smith | 210/195 R X |
| 3,814,249 | 6/1974 | Eaton | 210/321 B X |
| 3,945,922 | 3/1976 | Jagusch et al. | 210/196 X |

Primary Examiner—Charles N. Hart
Assistant Examiner—Robert H. Spitzer
Attorney, Agent, or Firm—Wenderoth, Lind & Ponack

[57] ABSTRACT

A hemodialysis system for use with any type of dialyzer, such as coil-type, Kiil-type and capillary-type or hollow fiber-type dialyzers, which has a fluid circulation circuit and a bypass circuit short-circuiting the fluid circulation circuit. At one junction between the fluid circulation circuit and the bypass circuit, an ejector is employed. The ejector has a nozzle, a diffuser axially aligned with the nozzle and defining an orifice and a suction chamber communicated with the orifice. During circulation of the dialysate in the circulation circuit and from the nozzle onto the diffuser of the ejector, a negative gauge pressure is developed in the suction chamber so that the dialysate can be drawn through the bypass circuit. The circulation circuit and the bypass circuit have respective coupling assemblies for removable connection with the coil-type dialyzer and with the Kiil-type or capillary-type, or hollow fiber-type, dialyzer.

13 Claims, 7 Drawing Figures

HEMODIALYSIS SYSTEM

The present invention generally relates to a hemodialysis system and, more particularly, to a hemodialysis system utilizable with any type of dialyzer such as a coil-type, Kiil-type and capillary-type or hollow fiber-type.

The importance and significance of a hemodialysis system used by patients suffering from for example, a kidney failure, are well recognized by those skilled in the art. It is also well known that a dialyzer used in hemodialysis, that is, an artificial kidney, is now available in a variety of types such as a coil dialyzer, Kiil or parallel flow dialyzer and capillary or hollow fiber dialyzer. These types of artificial kidneys have different constructions, but have such common features that they are substantially two chambers partitioned from each other by a semi-permeable membrane, one chamber, i.e., a blood chamber, for the flow of blood to be dialyzed and the other chamber, i.e., a dialysate chamber, for the flow of dialysate, and that there must be a pressure difference between the blood flowing through the blood chamber and the dialysate flowing through the dialysate chamber, that is, the pressure of the blood flowing through the blood chamber must be higher than that of the dialysate flowing through the dialysate chamber in order to remove excess water from said blood. More specifically, where a coil dialyzer is employed, the blood to be dialyzed is pumped under positive gauge pressure through the blood chamber while the dialysate is pumped through the dialysate chamber under a pressure equal to or approximating to the atmospheric pressure.

On the other hand, where a Kiil or capillary or hollow fiber dialyzer is utilized, the blood to be dialyzed is allowed to flow under its own pressure, that is, the blood pressure, through the blood chamber while the dialysate is pumped through the dialysate chamber under a negative gauge pressure, that is, a pressure lower than the blood pressure.

However, the required rate of flow of the dialysate through the dialysate chamber per unit time for a sufficient hemodialysis to be performed varies with the type of dialyzer employed. By way of example, in the case of the coil-type dialyzer, the required rate of flow of the dialysate through the dialysate chamber thereof is generally considered to be several liters per minute while, in the case of the Kiil-type dialyzer or the capillary- or hollow fiber-type dialyzer the required rate of flow of the dialysate through the dialysate chamber thereof is generally considered to be not less than half a liter per minute.

Despite the features common to all of these types of dialyzers, the manner by which the pressure difference is produced which is necessary to cause waste products of metabolism contained in the blood flowing through the blood chamber to be diffused through the semi-permeable membrane into the dialysate flowing through the dialysate chamber varies with the type of dialyzer. Moreover, so far as the required rate of flow of the dialysate through the dialysate chamber per unit time for sufficient hemo-dialysis is concerned, the coil-type dialyzer differs from the Kiil-type and capillary-type or hollow fiber-type dialyzer. Therefore, it has heretofore been a common practice to employ a particular hemodialysis system including a fluid circuit suited for use with a particular type of dialyzer. This means that unless a certain medical establishment, such as a hospital or a clinic, is furnished with various hemodialysis systems each suited for use with a particular type of dialyzer, the freedom of choice of the right hemodialysis system suited to a patient suffering from a particular kidney failure is limited.

On the other hand, for medical establishment to be furnished with various hemodialysis systems for the different types of dialyzers requires not only a relatively large space for installation and a large expenditure of money necessary to purchase them, but also an increase of the maintenance costs.

Apart from a dialyzer, generally two types of hemodialysis systems are now available, one being referred to as a "recirculating" hemodialysis system and the other being referred to as a "single-pass" hemodialysis system. While in the single-pass system, a dialysate once supplied from a source thereof through the dialyzer is discarded, the recirculating system is such that the dialysate supplied from a source thereof through the dialyzer is partly or wholly returned to the source for subsequent use.

In any event, whenever a particular hemodialysis system employs any one of the types of dialyzers or a particular type of dialyzer is employed in any one of the types of hemodialysis systems, the conventional hemodialysis system is complicated. In other words, the conventional hemodialysis system, either the single-pass type or the recirculating type, requires at least two pumping devices and various fluid-operated and hydromechanical elements associated therewith and, because of the complication in the system construction, complicated handling procedures are required.

According to the present invention, there is provided an improved, versatile hemodialysis system which satisfactorily and effectively operates with any type of dialyzer, which system is constructed with a minimum number of fluid-operated and hydromechanical elements which do not require any complicated handling prodedures, thereby substantially eliminating the disadvantages and inconveniences inherent in the conventional hemodialysis systems. More specifically, the hemodialysis system according to the present invention comprises a fluid circulating circuit, including a source of dialysate, an ejector having a nozzle and a diffuser aligned with said nozzle with an annular orifice defined between said nozzle and said diffuser, and a pumping device by which the dialysate is circulated through said circulating circuit. The system of the present invention further comprises a fluid bypass circuit having one end fluid-coupled to a source of dialysate, which may be the same as that in the fluid circulating circuit, and the other end fluid-coupled to a suction port of the ejector which leads to a suction chamber in communication with the annular orifice.

A fluid coupling assembly composed of a coupling socket and a coupling plug releasably connectable to said coupling socket is provided on each of the fluid circulating circuit and the bypass circuit.

A dialyzer of any of the foregoing types usable in the system of the present invention may be of any known construction. However, for the purpose of the present invention, the dialyzer should have a coupling socket secured to an intake port leading to the dialysate chamber and a coupling plug secured to an outlet port leading from the same dialysate chamber.

In the hemodialysis system according to the present invention, where the dialyzer to be used in the system is a type which includes a blood chamber through which the blood to be dialyzed is pumped under positive gauge pressure and a dialysate chamber through which the dialysate is supplied under a pressure equal to or approximating to the atmospheric pressure, such as a coil-type dialyzer, the socket and plug of the fluid coupling assembly on the bypass circuit are coupled to each other while the socket and plug of the fluid coupling assembly on the fluid circulation circuit are disconnected from each other to accommodate the dialyzer between said socket and plug of said assembly on said circulation circuit. At this time, the fluid bypass circuit may be interrupted by the use of any suitable switching valve such as a stopcock disposed in the bypass circuit.

On the other hand, where the dialyzer to be used in the system a present invention is of the type which includes a blood chamber through which the blood to be dialyzed is allowed to flow under the blood pressure and a dialysate chamber through which the dialysate is supplied under a negative gauge pressure lower than the blood pressure, such as the Kiil-type the capillary-type or the hollow fiber-type dialyzers, the socket and plug of the fluid coupling assembly on the circulation circuit are coupled to each other while the socket and plug of the fluid coupling assembly of the fluid bypass circuit are disconnected from each other to accommodate the dialyzer between said socket and plug of said coupling assembly of said bypass circuit. In this case, the dialysate from the dialysate source is supplied through the dialysate chamber of the Kiil-type or capillary-type or hollow fiber-type dialyzer by the effect of a negative gauge pressure developed in the suction chamber of the ejector as the dialysate pumped by the pumping device flows from the nozzle into the diffuser of the ejector, which negative gauge pressure so developed is created on the outlet side of the dialysate chamber of the particular dialyzer.

The circulation circuit in the system of the present invention may have an exhaust pipe line through which a portion of the dialysate containing waste products of metabolism is discarded. If this exhaust pipe line is employed while the source of the dialysate in the circulation circuit is constituted by a storage tank, the storage tank must contain the dialysate in at least an amount equal to or greater than the total amount of that portion of the dialysate discarded through the exhaust pipe line because it contains waste products of metabolism. Alternatively, if the source of the dialysate associated with the circulation circuit comprises a storage tank or container and a dialysate supply system including a supply pump for supplying the dialysate from said tank or container into the circulation circuit, the source of the dialysate may be disposed externally of the circulation circuit, in which case the amount of that portion of the dialysate to be discarded through the exhaust pipe line because it contains the waste products of metabolism is approximately equal to the amount of fresh dialysate pumped by the supply pump from the tank or container to said circulation circuit.

In any event, the employment of the ejector in the system of the present invention makes it possible to utilize at least a pumping device in the hemodialysis system.

The source of the dialysate from which the dialysate is supplied into the bypass circuit may be a storage tank disposed between the exit side of the ejector and the suction side of the pumping device or the exit side of the ejector to which the storage tank is fluid-coupled through the pumping device.

These and other objects and features of the present invention will readily become apparent from the following description taken in conjunction with preferred embodiments thereof with reference to the accompanying drawings, in which.

Before the description of the present invention proceeds, it is to be noted that like parts are designated by like reference numerals throughout the accompanying drawings.

Figure 1:
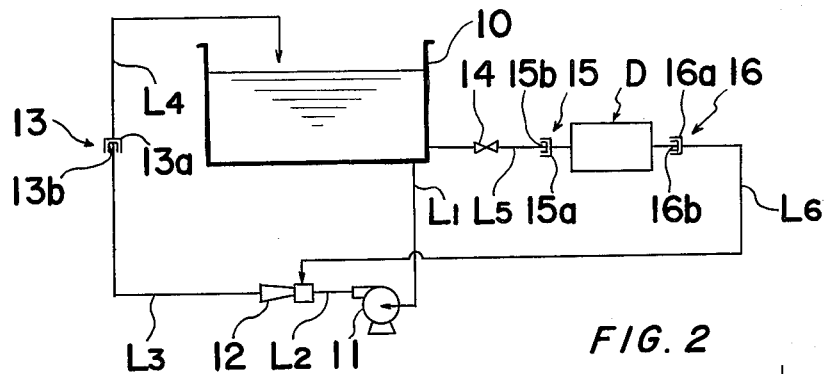
FIG. 1 is a schematic fluid circuit diagram of a hemodialysis system according to a first preferred embodiment of the present invention, which system is shown as using a Kiil-type of capillary- or hollow fiber-type dialyzer.

Referring first to FIG. 1, the hemodialysis system is shown to have a storage tank 10 for containing a predetermined dialysate therein. The tank 10 is fluid-connected to a pump 11 by means of a first pipe line L1 having one end opening out of the bottom of said tank 10 and the other end in communication with the suction port of said pump 11. The discharge port of the pump 11 is connected through a second pipe line L2 to an ejector 12 having a construction, which will be described later, which is in turn connected to the storage tank 10 by means of a third and fourth pipe lines L3 and L4 which are releasably coupled to each other by a fluid coupling assembly 13 constituted by a coupling socket 13a and a coupling plug 13b. In the construction thus far described, the dialysate within the tank 10 is, when the pump 11 is operated, sucked into the pump by way of the suction port thereof, then discharged from said pump 11 by way of the exhaust port thereof towards the ejector 12 through the second pipe line L2 and finally from the ejector 12 back to the storage tank 10 through the third and fourth pipe lines L3 and L4.

Figure 2:
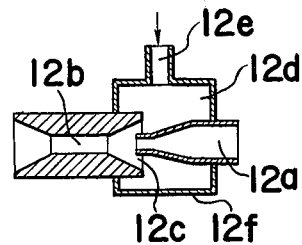
FIG. 2 is a schematic side sectional view of an ejector employed in the system of the present invention.

The details of the ejector 12 are illustrated schematically in FIG. 2. With reference to FIG. 2, the ejector 12 is shown to have nozzle 12a, coupled to the exhaust port of the pump 11 through the second pipe line L2, and a diffuser 12b having one end coupled to the third pipe line L3 and the other end substantially overhanging the nozzle 12a to define an annular orifice 12c, all of these elements being supported in position by a casing 12f with said nozzle 12a and diffuser 12b held in communication through said annular orifice 12c with an interior suction chamber 12d which is defined within said casing 12f. This ejector 12 is so designed that, during circulation of the dialysate from the tank 10 back to said tank 10 through the pump 11 and then the ejector 12 which is effected by the operation of the pump 11, a negative gauge pressure is developed in the annular orifice 12c as the dialysate under pressure flows from the nozzle 12a into the diffuser 12b, which negative gauge pressure thus developed acts to draw the dialysate into the suction chamber 12d through a suction port 12e, formed in the casing 12f and in communication with said chamber 12d, in a manner as will be described later.

Referring to FIG. 1, the coupling assembly 13 constituted by the coupling socket 13a and plug 13b may be of any known construction and may be of a type commercially available and sold under the trade name, "COUPLER Model-SP" manufactured by Nitto Koki K. K. (Japan). However, the present invention, the commercially available coupling assembly should either be made of a material chemically inert to the composition of the dialysate or have at least the portions which contact the dialysate flowing therethrough coated or lined with a material chemically inert to the composition of the dialysate.

Extending outwardly from the tank 10 adjacent the bottom thereof is a fifth pipe line L5 having a flow regulator 14, such as a needle valve or a restrictive orifice, disposed therein. This pipe line L5 is shown as being connected to the suction port 12e of the ejector 12 through a dialyzer D by way of a sixth pipe line L6. It is to be noted that the fluid circuit defined by the fifth and sixth pipe lines L5 and L6 may be considered as a bypass circuit relative to the circulation circuit constituted by the first to fourth pipe lines L1 to L4.

In FIG. 1, the dialyzer D is either a capillary- or hollow fiber-type or of a Kiil-type and, for the purposes of the present invention, is shown as having a coupling socket 15a and a coupling plug 16b respectively secured to the inlet and outlet of the dialysate chamber of said dialyzer D. This dialyzer D is disposed in the bypass circuit with the coupling socket 15a receiving a coupling plug 15b in the fifth pipe line L5 on one hand and the coupling plug 16b inserted into a coupling socket 16a on the sixth pipe line in the other hand. It is to be noted that a fluid coupling assembly 15 constituted by the socket 15a on the intake side of the dialysate chamber of the dialyzer D and the plug 15b in the fifth pipe line L5 and a fluid coupling assembly 16 constituted by the socket 16a in the sixth pipe line L6 and the plug 16b on the outlet side of the dialysate chamber of the dialyzer D are identical in size and construction with each other so that when the dialyzer D is removed from the bypass circuit, the pipe line L5 can be coupled to the pipe line L6 with the plug 15b inserted into the socket 16a. The coupling assemblies 15 and 16 may be of a construction identical to the coupling assembly 13, and may have the same or different size in relation to said coupling assembly 13.

Where a coil-type dialyzer (not shown) is to be employed in the system of the present invention in place of the capillary- or hollow fiber-type or of Kiil-type dialyzer D, the coil-type dialyzer is fluid-coupled in position between the socket 13a and the plug 13b in the circulation circuit. In order to achieve this, the dialyzer must have a coupling socket (not shown), which can be mated to the coupling plug 13b and is secured to the inlet of the dialysate chamber thereof, and a coupling plug (not shown) which can be mated to the coupling socket 13a and secured to the outlet of the dialysate chamber thereof. It will readily be seen that installation of the coil-type dialyzer in the portion of the fluid circulation circuit between the ejector 12 and the storage tank 10 can be carried out by first disconnecting the socket 13a and the plug 13b from each other and then connecting the plug and socket provided in the coil-type dialyzer to the socket 13a and plug 13b, respectively. In such case, the capillary- or hollow fiber-type or Kiil-type dialyzer D is removed from the bypass circuit and the socket 16a and the plug 15b are connected to each other. Alternatively, without the dialyzer D being removed, either or both of the pipe lines L5 and L6 may have a stopcock which is then closed. Furthermore, any one of the elements of the coupling assembly 13, constituted by the coupling socket 13a and plug 13b and the coupling assembly constituted by the coupling socket 16a and plug 15b may be of a type wherein either the socket or plug has a built-in check valve operable to close upon disconnection between the socket and its mating plug and to open upon insertion of the plug into the socket.

The ejector 12 performs its most significant role when the dialysis system makes use of the Kiil-type or capillary- or hollow fiber-type dialyzer D as shown in FIG. 1. More specifically, the negative gauge pressure is developed in the annular orifice 12c and then in the suction chamber 12d as the dialysate flows from the nozzle 12a into the diffuser 12b under pressure, as hereinbefore described. Accordingly, when the negative gauge pressure is thus developed in the suction chamber 12d, it develops equally in the sixth pipe line L6 and, therefore, by the effect of the negative gauge pressure thus developed, the dialysate fed from the storage tank 10 to the coupling assembly 15 through the flow regulator 14 is drawn through the dialysate chamber of the dialyzer D into the sixth pipe line L6 and then towards the suction chamber 12d of the ejector 12. The dialysate thus drawn through the dialysate chamber contains waste products of metabolism diffused from the blood chamber of the dialyzer D, through which the blood being dialyzed flows, into the dialysate flowing through the dialysate chamber of the dialyzer D. The dialysate thus drawn into the suction chamber 12d through the sixth pipe line L6 is then directed towards the third pipe line L3 through the annular orifice 12c and then the diffuser 12b joining the jet of dialysate flowing from the nozzle 12a onto the diffuser 12b.

Where a coil-type dialyzer is employed in place of the dialyzer D, the bypass circuit from the tank 10 to the ejector 12 performs no significant role and, therefore, as hereinbefore described, the flow of the dialysate through the bypass circuit may be interrupted in the manner described.

Although in the embodiment of FIG. 1, the pipe line L5 has been described as extending from the tank 10 adjacent the bottom thereof, the location may not always be limited thereto, but it may be coupled to the first pipe line L1. Alternatively, the fifth pipe line may be coupled to the third pipe line L3, as indicated by L5' in FIGS. 5 and 6 so that the dialysate discharged from the ejector 12 can be fed in part to the tank 10 through the fourth pipe line L4 and in part to the dialysate chamber of the dialyzer D.

Figure 3:
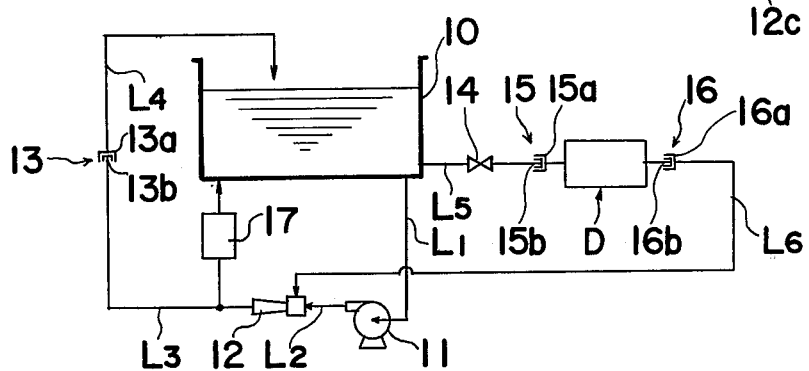
FIG. 3 is a view similar to FIG. 1, showing a second preferred embodiment of the present invention.
Figure 4:
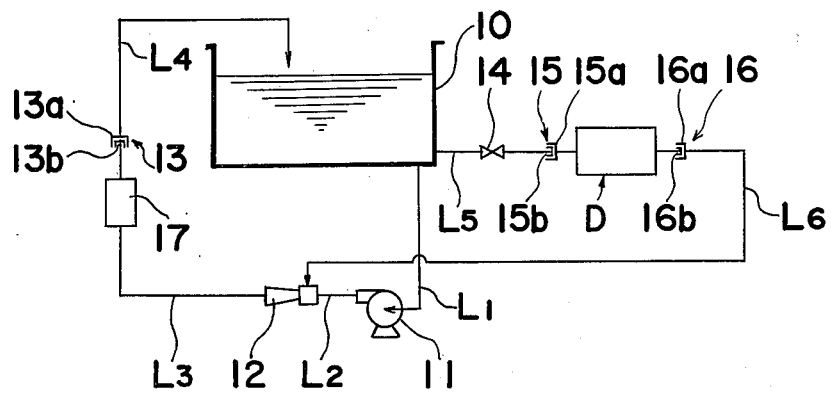
FIG. 4 is a view similar to FIG. 1, showing a third preferred embodiment of the present invention.
Figure 6:
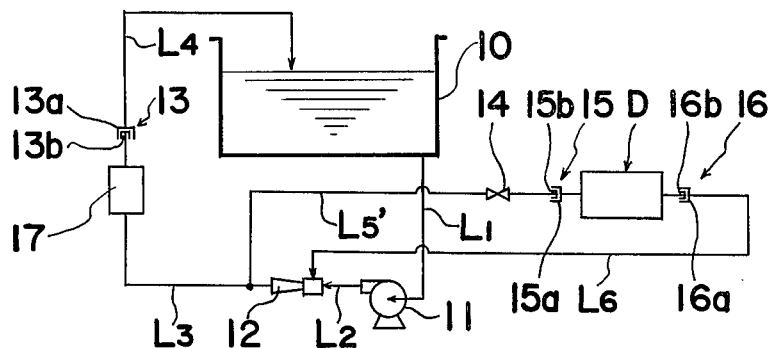
FIG. 6 is a view similar to FIG. 1, showing a fifth preferred embodiment of the present invention.

In the dialysis system of the present invention, a known adsorbent unit may be employed such as shown in FIGS. 3, 4 and 6, for partly or wholly adsorbing the waste products carried by the dialysate flowing therethrough. In the embodiment of FIG. 3, the adsorbent unit 17 is shown to be disposed between the third pipe line L3 and the tank 10 so that the dialysate emerging from the ejector 12 can be fed to the tank 10 partly through the fourth pipe line L4 and partly through said adsorbent unit 17. Alternatively, if the pipe line L3 is branched with one part connected to the pipe line L4 and the other part to the bottom of the tank 10, the adsorbent unit may be removably submerged in the dialysate within the tank 10, in which case the intake port of the adsorbent unit must be coupled through the tank bottom to the branch pipe bifurcating from the pipe line L3.

Figure 5:
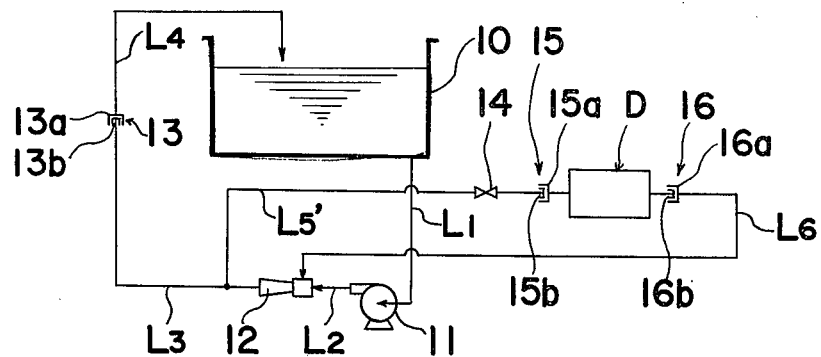
FIG. 5 is a view similar to FIG. 1, showing a fourth preferred embodiment of the present invention.

Furthermore, in the system of FIG. 5, it is possible to dispose the adsorbent unit in the manner as shown in FIG. 3. If the adsorbent unit disposed in the manner as shown in FIG. 4 is used in the system of FIG. 5, it is obvious that the system shown in FIG. 6 is established.

The present invention will now be further explained way of example.

The inventors have conducted a series of experiments with the system having the construction shown in FIG. 3 wherein a centrifugal pump for experimental use was employed for the pump 11 and wherein the nozzle 12a of the ejector 12 had a nozzle outlet with an inner diameter of 4.5 mm. When the centrifugal pump was operated so as to discharge the dialysate in an amount of 15 liters per minute, a pressure of about 280 Torr was obtained at the outlet of the dialysate chamber of the dialyzer D, at which time the rate of flow of the dialysate through the sixth pipe line L6 was 500 milliliter per minute. The discharge pressure of the centrifugal pump was 0.5 kg/cm²G.

When the dialyzer D was replaced by a coil-type dialyzer, the plug 15b was directly coupled to the socket 16a, and the coil-type dialyzer was installed between the socket 13a and the plug 13b, and the amount of the dialysate discharged from the ejector 12 was found to be 15.5 liters per minute. However, of this amount discharged from the ejector 12, 500 milliliter per minute was fed to the tank 10 through the adsorbent unit 17 and the remaining 15 liters per minute was fed to the tank 10 through the coil-type dialyzer.

Figure 7:
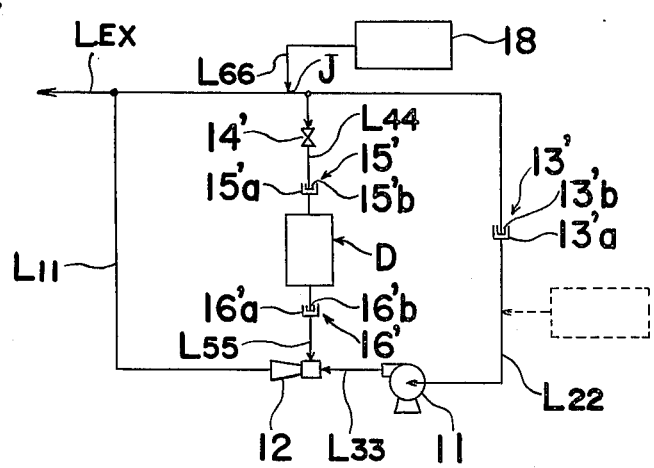
FIG. 7 is a view similar to FIG. 1, showing a sixth preferred embodiment of the present invention.

In the embodiment of FIG. 7, the fluid circulation circuit includes a first pipe line L11, having one end coupled to the discharge port of the ejector 12 and the other end coupled to the coupling plug 13'b, a second pipe line L22 having one end coupled to the suction port of the pump 11 and the other end coupled to the coupling socket 13'a which is coupled to said plug 13'b when no coil-type dialyzer is employed as shown, and a third pipe line L33 extending between the discharge port of the pump 11 and the suction nozzle 12a of the ejector 12. It will, therefore, readily be seen that the dialysate from a source of dialysate 18 can, during operation of the pump 11, be circulated through the pipe lines L11, L22 and L33.

The circulation circuit has an exhaust pipe line Lex for discharging a portion of the dialysate being circulated at a rate substantially approximately equal to the rate of supply of a fresh dialysate from the source of dialysate 18 into the circulation circuit. the exhaust pipe line Lex in the embodiment of FIG. 7 is shown as being coupled to the first pipe line L11, but may be coupled to the discharge port of the ejector 12 or the second pipe line L22.

The bypass circuit in the system of FIG. 7 includes a fourth pipe line L44 having a flow regulator 14' disposed therein, one end of which is coupled to the circulation circuit and, particularly, to the first pipe lien L11 and the other end has the coupling plug 15'b secured thereto and a fifth pipe line L55 having one end coupled to the suction port 12e of the ejector 12 and the other end having the coupling socket 16a secured thereto. The bypass circuit is shown as having Kiil-type or capillary-type dialyzer D coupled between the plug 15'b and the socket 16'a, said plug 15'b being fluid coupled to the socket 15'a extending from the intake port of the dialysate chamber of the dialyzer D while the socket 16'a receives the plug 16'b extending from the outlet port of the same dialysate chamber of the dialyzer D.

The source of dialysate 18 may comprise a storage tank having a size sufficient to accommodate a necessary amount of dialysate determined in consideration of the total amount of the dialysate exhausted through the exhaust pipe line Lex, which storage tank may be so designed and disposed that the dialysate within the storage tank can be supplied to the circulation circuit under hydrostatic pressure, i.e., by the effect of its own head within the storage tank. Alternatively, where it is not desired to supply the dialysate under hydrostatic pressure, that is, by the effect of its own head within a container in which the dialysate is accommodated, the source of dialysate 18 may comprise a dialysate supply unit including a supply pump. If the dialysate supply unit including the supply pump is employed, the supply unit may be fluid-coupled to the circulation circuit at a junction J through a supply pipe line L66 as shown by the solid line in FIG. 7 or to the pipe line L22 as shown by the broken line in FIG. 7.

The hemodialysis system shown in FIG. 7 satisfactorily operates in a substantially similar manner as the hemodialysis system according to any of the embodiments of FIGS. 1 to 6, but differs from them in that a portion of the dialysate discharged from the ejector 12 is exhausted in the system of FIG. 7. In practice, the total amount of the dialysate discarded through the exhaust pipe line Lex must be controlled to be approximatly equal to the total amount of the dialysate supplied from the source of dialysate 18. This can readily be achieved by the employment of suitable control instruments for controlling the pressure or flow rate of the dialysate flowing through the system in response to, for example, a reduction of the amount of the dialysate within the dialysate source or a variation in the amount of the dialysate being discarded through the exhaust pipe line Lex.

Even in the system of FIG. 7, the employment of an adsorbent unit of any known construction is possible. If the adsorbent unit is employed, although not shown, it may be disposed either in the first pipe line L11 or in the fifth pipe line L55. However, since the system of FIG. 7 is such that a portion of the dialysate discharged from the ejector 12 is discarded while the fresh dialysate in an amount approximately corresponding to the amount of that portion of the dialysate being discarded is supplied from the dialysate source, the system of FIG. 7 does not require the use of an adsorbent unit as much as in the system of any of the foregoing embodiments. In any even, if the adsorbent unit is employed, the amount of the dialysate to be discarded may be reduced which results in reduction of the amount of the fresh dialysate to be supplied from the dialysate source.

Although the present invention has fully been described by way of example with reference to the accompanying drawings, it is to be noted that various changes and modifications will be apparent to those skilled in the art. For example, while in the embodimens of FIGS. 1, 3, 4 and 7 a single source of dialysate has been described as supplying the dialysate in part to the circulation circuit and in part to the bypass circuit and while in the embodiments of FIGS. 5 and 6 a source of dialysate to be supplied into the bypass circuit has been described as constituted by the pipe line L3, an additional source of dialysate may be employed. More specifically, if an additional source of dialysate is employed while the source of dialysate such as indicated by 10 or 18 is employed for supplying the dialysate into the circulation circuit as shown, the additional source of dialysate may be fluid-coupled to the pipe line L5, L5' or L44. In particular, in the embodiment of FIG. 7, if the source of dialysate is directly fluid-coupled to the socket 15'a, the source of dialysate which has been described and indicated by 18 may be omitted.

Furthermore, while the conventional hemodialysis system utilizing the Kiil-type or capillary- or hollow fiber-type dialyzer requires the employment of a specially designed pump because of the negative gauge pressure it must develop which negative gauge pressure is necessary to draw the dialysate through the dialysate chamber of the dialyzer, any commercially available pump, may be employed for the pump 11 as long as a predetermined discharge pressure and a predetermined flow rate can be attained thereby. Of these various types of pumps, a centrifugal pump is preferred because of the handling ease, compactness and light-weight.

Therefore, these changes and modifications are to be understood as included within the true scope of the present invention unless they depart therefrom.

What is claimed is:

1. A dialysate circulating system which can be made into a hemodialysis system by the addition of a dialyzer, said circulating system comprising, in combination:
    a source of dialysate;
    a fluid circulating circuit having one end connected to said source of dialysate for circulating the dialysate supplied from the source of dialysate along said fluid circulating circuit;
    an ejector in said fluid circulating circuit and having an inlet nozzle, a diffuser axially aligned with said inlet nozzle and defining an orifice in cooperation with said nozzle and a suction chamber in communication with said orifice, said ejector being positioned in said circulating circuit for directing the dialysate being circulated from the nozzle into the diffuser for developing a negative gauge pressure in said suction chamber;
    first and second mating coupling members in said fluid circulating circuit connectable to each other and being disposed in said circulating circuit downstream of said ejector in terms of the direction of flow of the dialysate;
    a fluid circuit means connected between said source of dialysate and said suction chamber of said ejector; and
    third and fourth mating coupling members in said fluid circuit means connectable to each other,
    said circulating system, when said third and fourth mating coupling members in said fluid circuit means are directly connected to each other, having therein a dialyzer of the type in which blood to be dialyzed is pumped through a blood chamber on one side of a semi-permeable membrane under a positive gauge pressure and dialysate is pumped through a dialysate chamber on the other side of the membrane under a pressure approximating or equal to atmospheric pressure with the opposite ends of the dialysate chamber connected between the first and second mating coupling members in said fluid circulating circuit and when the first and second mating coupling members are directly connected to each other, having therein a dialyzer of the type in which blood to be dialyzed is allowed to flow under the natural pressure thereof through a blood chamber on one side of a semi-permeable membrane and dialysate is caused to flow through dialysate chamber on the other side of the membrane under negative gauge pressure with the opposite ends of the dialysate chamber connected between the third and fourth coupling members in said fluid circuit means.

2. A hemodialysis system as claimed in claim 1, wherein said source of dialysate is a storage tank accommodating therein a predetermined amount of dialysate and said circulating means comprises a pump having a suction port in communication with said storage tank and a discharge port in communication with the nozzle of said ejector, said circulating circuit being constituted by a first passage extending between said tank and said suction port of said pump, a second passage extending between said discharge port of said pump and said nozzle, a third passage extending between said diffuser and said first coupling and a fourth passage extending between said second coupling and said tank, and wherein said circuit means is constituted by a first bypass passage extending between said source of dialysate and said third coupling and a second bypass passage extending between said fourth coupling and said suction chamber of said ejector.

3. A dialysate circulating system as claimed in claim 1 in which the downstream end of said fluid circulating circuit opens into said source of dialysate.

4. A dialysate circulating system as claimed in claim 1 in which said fluid circulating circuit has an exhaust branch branching therefrom for discharging a portion of the dialysate being circulated.

5. A dialysate circulating system as claimed in claim 1 further comprising an adsorbent means connected in series in said fluid circulating circuit between said ejector and said first and second coupling members.

6. A dialysate circulating system as claimed in claim 1 further comprising an adsorbent means connected from said fluid circulating circuit at a point between said ejector and said first and second coupling members and said source of dialysate.

7. A dialysate circulating system as claimed in claim 1 in which said fluid circuit means has a cutoff valve means therein for cutting off flow therethrough.

8. A dialysate circulating system which can be made into a hemodialysis system by the addition of a dialyzer, said circulating system comprising, in combination:
    a source of dialysate;
    a fluid circulating circuit having one end connected to said source of dialysate for circulating the dialysate supplied from the source of dialysate along said fluid circulating circuit;
    an ejector in said fluid circulating circuit and having an inlet nozzle, a diffuser axially aligned with said inlet nozzle and defining an orifice in cooperation with said nozzle and a suction chamber in communication with said orifice, said ejector being postioned in said circulating circuit for directing the dialysate being circulated from the nozzle into the diffuser for developing a negative gauge pressure in said suction chamber;
    first and second mating coupling members in said fluid circulating circuit connectable to each other and being disposed in said circulating ciruit downstream of said ejector in terms of the direction of flow of the dialysate;

a fluid circuit means connected between said fluid circulating circuit downsteam of said ejector and said suction chamber of said ejector; and third and fourth mating coupling members in said fluid circuit means connectable to each other, said circulating system, when said third and fourth mating coupling members in said fluid circuit means are directly connected to each other, having therein a dialyzer of the type in which blood to be dialyzed is pumped through a blood chamber on one side of a semi-permeable membrane under a positive gauge pressure and dialysate is pumped through a dialysate chamber on the other side of the membrane under a pressure approximating or equal to atmospheric pressure with the opposite ends of the dialysate chamber connected between the first and second mating coupling members in said fluid circulating circuit and when the first and second mating coupling members are directly connected to each other, having therein a dialyzer of the type in which blood to be dialyzed is allowed to flow under the natural pressure thereof through a blood chamber on one side of a semi-permeable membrane and dialysate is caused to flow through a dialysate chamber on the other side of the membrane under a negative gauge pressure with the opposite ends of the dialysate chamber connected between the third and fourth coupling members in said fluid circuit means.

9. A dialysate circulating system as claimed in claim 8 in which the downstream end of said fluid circulating circuit opens into said source of dialysate.

10. A dialysate circulating system as claimed in claim 8 in which said fluid circulating circuit has an exhaust branch branching therefrom for discharging a portion of the dialysate being circulated.

11. A dialysate circulating system as claimed in claim 8 further comprising an adsorbent means connected in series in said fluid circulating circuit between said ejector and said first and second coupling members.

12. A dialysate circulating system as claimed in claim 8 in which said fluid circuit means has a cutoff valve means therein for cutting off flow therethrough.

13. A hemodialysis system as claimed in claim 8 wherein said source of dialysate is a storage tank accommodating therein a predeteremined amount of dialysate and said circulating means comprises a pump having a suction port in communication with said storage tank and a discharge port in communication with the nozzle of said ejector, said circulating circuit being constituted by a first passage extending between said tank and said suction port of said pump, a second passage extending between said discharge port of said pump and said nozzle, a third passage extending between said diffuser and said first coupling and a fourth passage extending between said second coupling sand said tank, and wherein said circuit means is constituted by a first bypass passage extending between said third passage and said third coupling and a second bypass passage extending between said fourth coupling and said suction chamber of said ejector.

* * * * *